United States Patent
Kerr et al.

(10) Patent No.: US 10,365,194 B2
(45) Date of Patent: Jul. 30, 2019

(54) HIGH TEMPERATURE DENSITOMETER DEVICE AND STEAM QUALITY MEASUREMENT METHOD AND DEVICE

(71) Applicant: Scientific Drilling International, Inc., Houston, TX (US)

(72) Inventors: Robert Peter Kerr, The Woodlands, TX (US); Brian Gleason, Atascadero, CA (US); Robert Moore, Paso Robles, CA (US); Adam Olzick, San Luis Obispo, CA (US); Bill Denzel, Templeton, CA (US)

(73) Assignee: SCIENTIFIC DRILLING INTERNATIONAL, INC., Houston, TX (US)

( * ) Notice: Subject to any disclaimer, the term of this patent is extended or adjusted under 35 U.S.C. 154(b) by 344 days.

(21) Appl. No.: 15/143,583

(22) Filed: Apr. 30, 2016

(65) Prior Publication Data
US 2016/0320280 A1 Nov. 3, 2016

Related U.S. Application Data

(60) Provisional application No. 62/155,848, filed on May 1, 2015.

(51) Int. Cl.
*G01N 9/00* (2006.01)
*G01N 9/36* (2006.01)
(Continued)

(52) U.S. Cl.
CPC .............. *G01N 9/002* (2013.01); *E21B 49/00* (2013.01); *G01N 33/2823* (2013.01);
(Continued)

(58) Field of Classification Search
CPC .. G01N 9/002; G01N 11/16; G01N 2009/006; G01N 2291/02827; G01N 9/24;
(Continued)

(56) References Cited

U.S. PATENT DOCUMENTS 4,526,480 A 7/1985 Ward
4,679,947 A * 7/1987 Miller ................... G01N 9/002
374/42

(Continued)

OTHER PUBLICATIONS

International Search Report and Written Opinion issued in PCT/US2016/030332, dated Aug. 5, 2016, 12 pages.
(Continued)

*Primary Examiner* — Randy W Gibson
*Assistant Examiner* — Gedeon M Kidanu
(74) *Attorney, Agent, or Firm* — Adolph Locklar

(57) ABSTRACT

A method for measuring two-phase mixture quality in a fluid may include providing a densitometer with a densitometer body, a resonator tine, a drive transducer, and a pickup transducer. The method may also include exposing the resonator tine to the fluid and oscillating the resonator tine with the drive transducer. In addition, the method may include measuring the oscillation of the resonator tine with the pickup transducer, and determining a density of the fluid based on the measured oscillation of the resonator tine. The method may also include determining a two-phase mixture quality based on the determined density.

42 Claims, 15 Drawing Sheets

(51) Int. Cl.
  *E21B 49/00* (2006.01)
  *E21B 49/08* (2006.01)
  *G01N 33/28* (2006.01)
(52) U.S. Cl.
  CPC .......... *E21B 2049/085* (2013.01); *G01N 9/36* (2013.01); *G01N 2009/006* (2013.01)
(58) Field of Classification Search
  CPC ...... G01F 15/024; G01F 15/046; G01F 15/08; G01F 1/74; G01F 1/8409; G01F 1/8413; G01F 1/8418; G01F 1/8431; G01F 1/8436; G01F 1/8468; G01F 1/849; G01Q 10/06
  See application file for complete search history.

(56) References Cited

U.S. PATENT DOCUMENTS

| | | | |
|---|---|---|---|
| 4,922,745 A | 5/1990 | Rudkin et al. | |
| 5,265,552 A * | 11/1993 | Taylor | B63G 8/39 114/219 |
| 6,378,364 B1 * | 4/2002 | Pelletier | E21B 47/06 73/152.47 |
| 7,360,453 B2 | 4/2008 | Riede et al. | |
| 7,552,619 B2 | 6/2009 | Andle | |
| 2002/0178803 A1 * | 12/2002 | Pelletier | E21B 47/06 73/152.47 |
| 2004/0221660 A1 * | 11/2004 | Dutton | G01F 1/74 73/861.354 |
| 2007/0186686 A1 * | 8/2007 | Drahm | G01F 1/8409 73/861.357 |
| 2009/0120169 A1 * | 5/2009 | Chandler, Jr. | G01N 9/002 73/54.41 |
| 2010/0170322 A1 * | 7/2010 | Van Cleve | G01F 1/74 73/1.16 |
| 2011/0023626 A1 * | 2/2011 | Weinstein | G01F 1/74 73/861.357 |
| 2012/0150452 A1 * | 6/2012 | Drobkov | G01N 9/002 702/25 |
| 2015/0070000 A1 * | 3/2015 | Gao | E21B 47/06 324/204 |

OTHER PUBLICATIONS

Groposo, et al. "Mud Density Prospection Using a Tuning Fork." Journal of Waterway, Port, Coastal, and Ocean Engineering,10.1061/(ASCE)WW.1943-5460.0000289, 2014 (7 pages).

* cited by examiner

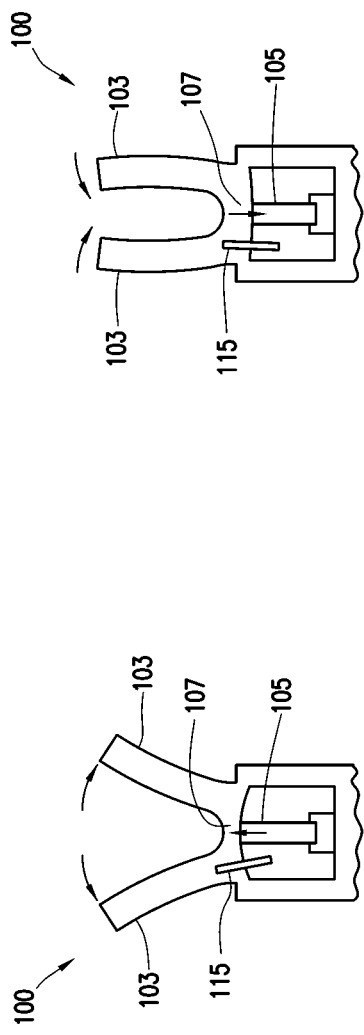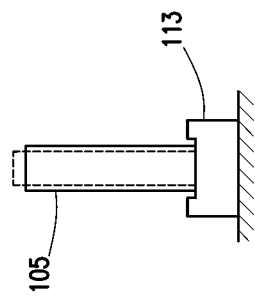
FIG. 3B
FIG. 4
FIG. 3A

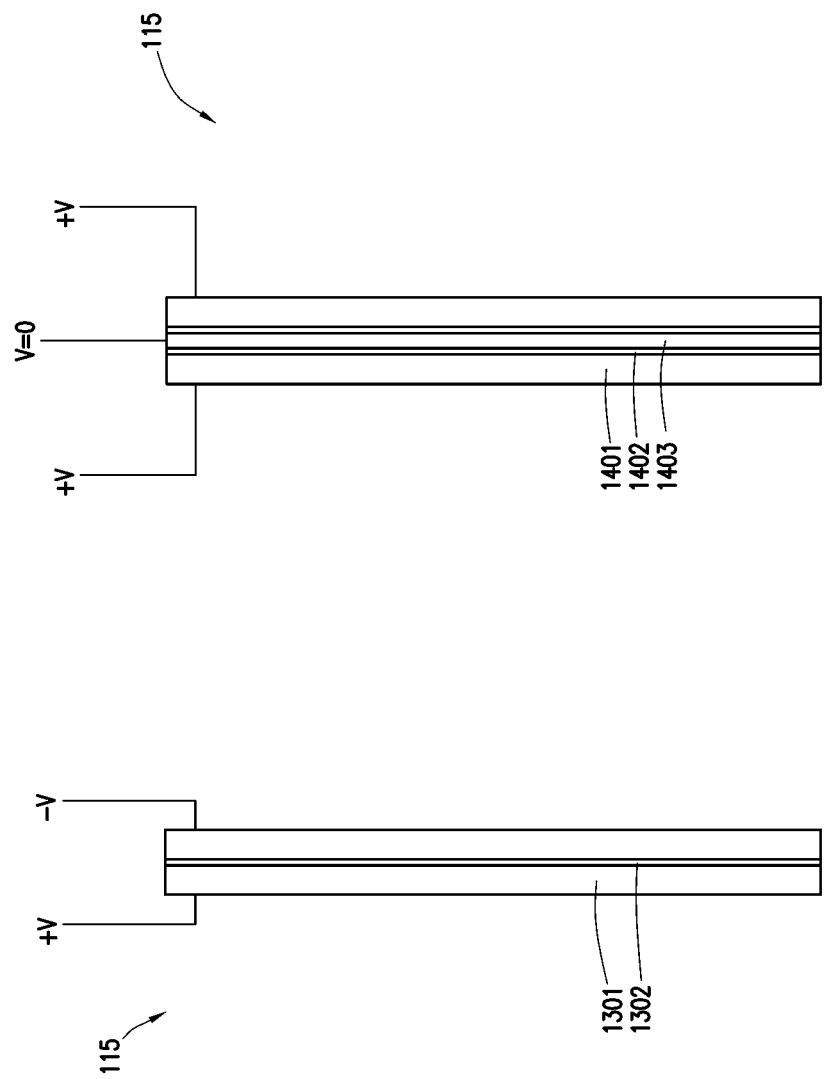

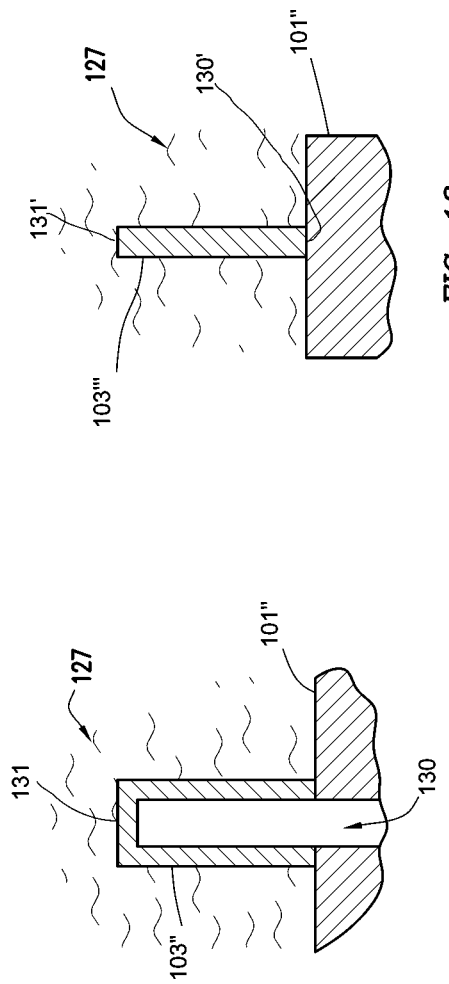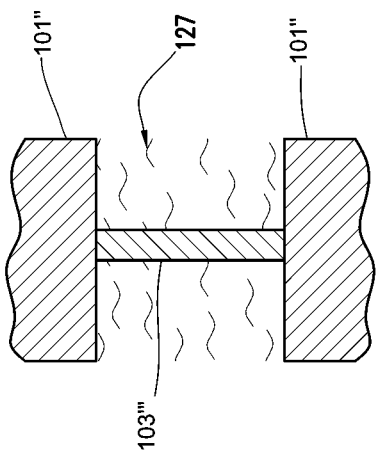

HIGH TEMPERATURE DENSITOMETER DEVICE AND STEAM QUALITY MEASUREMENT METHOD AND DEVICE

CROSS-REFERENCE TO RELATED APPLICATIONS

This application is a non-provisional application which claims priority from U.S. provisional application No. 62/155,848, filed May 1, 2015, which is incorporated by reference herein in its entirety.

TECHNICAL FIELD/FIELD OF THE DISCLOSURE

The present disclosure relates to devices and methods for steam quality measurement.

BACKGROUND

Densitometer sensors may be used for measuring the density of fluids. These fluids may be liquids, gases, mixtures of liquids and gases, and may also include small particles of suspended solids. Densitometers may be used in monitoring and/or controlling various industrial, manufacturing, or medical processes. Densitometers may also be deployed in oil and gas wellbores as a production logging instrumentation sensor, thereby allowing for a density measurement to be made at different depths within a wellbore. In wellbore applications, densitometer measurements may provide data that may be used to determine the type of fluid in or gas in the wellbore and may be used for water detection.

Due to the earth's geothermal temperature gradient, densitometers deployed in wellbore applications often operate at the high temperatures encountered as the depth of the wellbore increases. Additionally, the geothermal temperature gradient is not constant across the earth's surface and may be higher in some areas of exploration and production, as in the Haynesville region of the United States. Thus, deep wellbores in which it may be desirable to obtain densitometer measurements may have high temperatures in excess of 350° F. Traditionally, due to the limitations of existing transducer technology often utilized in densitometers, existing densitometers do not operate above 350° F. and are therefore limited in the wellbore depths or regions in which the densitometers may be deployed.

Quality, Q, of two-phase liquid-vapor mixture is a parameter that defines the proportion of a saturated vapor in the two-phase liquid-vapor mixture. One example of a two-phase liquid-vapor mixture may be steam. Given a mixture consisting of saturated liquid and saturated vapor phases, Q may be defined as the mass of the vapor, $m_{vapor}$, divided by the total mass of the two phase mixture, $m_{liquid}+m_{vapor}$.

$$Q = \frac{m_{vapor}}{m_{liquid} + m_{vapor}}$$

With knowledge of the thermodynamic properties of a two-phase liquid-vapor mixture, Q may be combined with the corresponding temperature or pressure measurement of the two-phase liquid-vapor mixture to compute the amount of heat energy or enthalpy of the two-phase liquid-vapor mixture.

Q, combined with pressure and/or temperature measurements, has conventionally been used for monitoring and controlling various industrial and manufacturing processes including power generation.

SUMMARY

The present disclosure provides for a method for measuring two-phase mixture quality in a fluid. The method includes providing a densitometer. The densitometer includes a densitometer body and a resonator tine. The resonator tine is mechanically coupled to the densitometer body. The densitometer further includes a drive transducer. The drive transducer is mechanically coupled to the resonator tine and positioned within the densitometer body. The densitometer also includes a pickup transducer. The pickup transducer is mechanically coupled to the resonator tine and positioned within the densitometer body. The method also includes exposing the resonator tine to the fluid and oscillating the resonator tine with the drive transducer. In addition, the method includes measuring the oscillation of the resonator tine with the pickup transducer, and determining a density of the fluid based on the measured oscillation of the resonator tine. The method also includes determining a two-phase mixture quality based on the determined density.

The present disclosure provides for a densitometer. The densitometer includes a densitometer body, a resonator tine, where the resonator tine is mechanically coupled to the densitometer body. The densitometer further includes a drive transducer, where the drive transducer is mechanically coupled to the resonator tine and positioned within the densitometer body. In addition, the densitometer includes a pickup transducer, where the pickup transducer is mechanically coupled to the resonator tine and positioned within the densitometer body.

The present disclosure provides for an apparatus. The apparatus includes a densitometer body, a resonator tine, where the resonator tine is mechanically coupled to the densitometer body. The apparatus further includes a drive transducer, where the drive transducer is mechanically coupled to the resonator tine and positioned within the densitometer body. In addition, the apparatus includes a pickup transducer, where the pickup transducer is mechanically coupled to the resonator tine and positioned within the densitometer body. The apparatus also includes a pressure or temperature monitor, the pressure or temperature monitor adapted to measure the pressure or temperature of a fluid. The apparatus includes a microprocessor, the microprocessor in electrical connection with the drive transducer and pickup transducer. The microprocessor includes non-transitory computer-readable storage medium, where the non-volatile memory includes a database of fluid thermodynamic properties.

BRIEF DESCRIPTION OF THE DRAWINGS

The present disclosure is best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

FIGS. 3A, 3B depict cross section views of the steam quality densitometer of FIG. 2.

FIG. 4 depicts a drive transducer of the steam quality densitometer of FIG. 2.

FIG. 11 depicts a transducer consistent with at least one embodiment of the present disclosure.

FIG. 12 depicts a transducer consistent with at least one embodiment of the present disclosure.

FIG. 17 depicts a portion of a resonator consistent with at least one embodiment of the present disclosure.

FIG. 18 depicts a portion of a resonator consistent with at least one embodiment of the present disclosure.

FIG. 19 depicts a portion of a resonator consistent with at least one embodiment of the present disclosure.

DETAILED DESCRIPTION

Figure 1A:
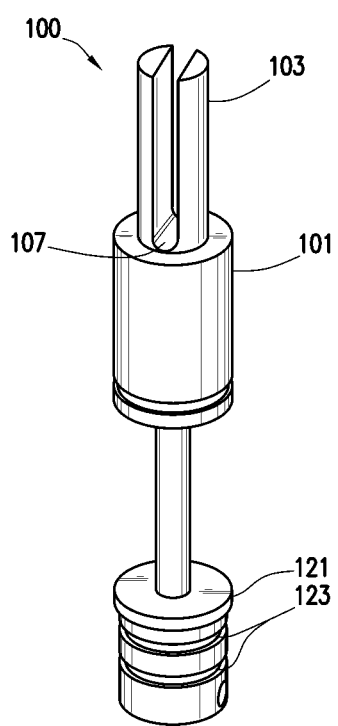
FIGS. 1A-1C are perspective views of a tuning fork densitometer consistent with at least one embodiment of the present disclosure.

It is to be understood that the following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed.

Densitometers may be used to measure the density and viscosity of a fluid. The fluid to be measured may include liquids, gases, or a multi-phase mixture of liquids and gases. In certain embodiments, the fluid may contain small particles of suspended solids. Vibrating densitometers may use one or more mechanical structures, where the movement or vibration of the one or more mechanical structures interacts with and moves the fluid. With attention to FIG. 1, resonator electronics 109 in densitometer 100 may measure the mechanical interaction between mechanical structures, such as, for example and without limitation, resonator tines 103 and the fluid and converts the measure of mechanical interaction into a density and/or viscosity measurement.

Figure 2:
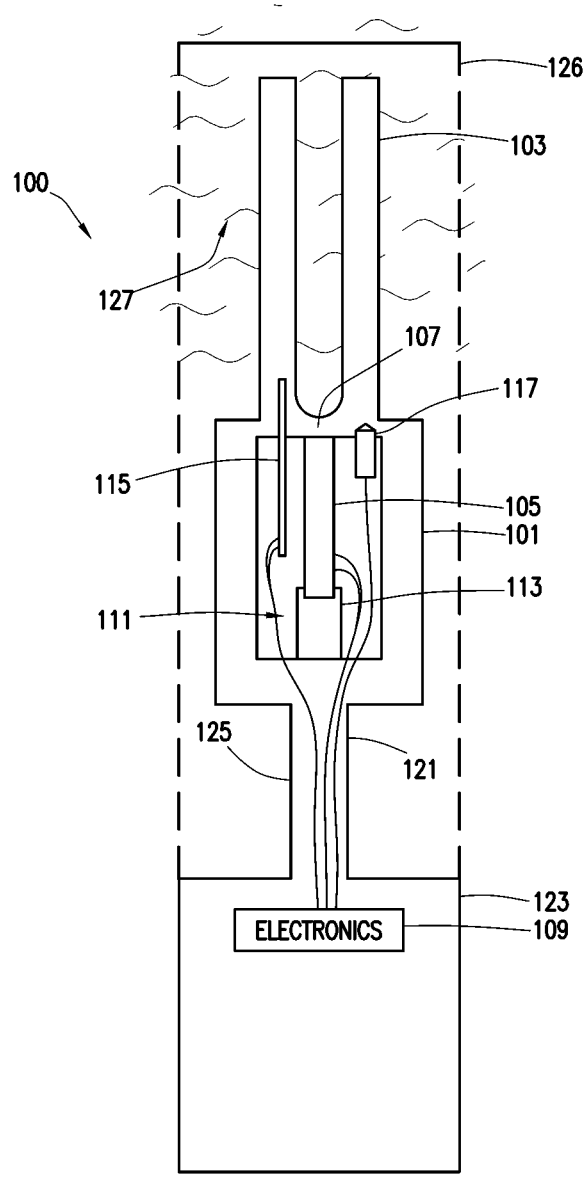
FIG. 2 is a cross section view of a steam quality densitometer consistent with at least one embodiment of the present disclosure.

The mechanical structures of the densitometer may be resonators or, in some embodiments, tines. In some embodiments, such as depicted in FIG. 2, pickup transducer 115 may be mechanically coupled to resonator tine 103. In some embodiments, pickup transducer 115 may be positioned at least partially within densitometer body 101. In certain embodiments, vibrating densitometers may include a drive transducer 105 that mechanically moves or vibrates one or more resonators, thereby causing dynamic fluid interaction between the resonator and the fluid. Vibrating densitometers may also include "pickup" transducer 115 to receive, detect, sense, or "pick up" a measure of the movement of the one or more resonators as the one or more resonators interact with the fluid. In some embodiments, the drive and pickup transducers may be the resonator itself. In some embodiments, a single transducer may be a drive transducer and a pickup transducer.

In some embodiments, the resonator may be immersed into or be directly part of a flow path of a fluid or sample of the fluid. The fluid may be in a wellbore. In those embodiments, the immersion of the resonator in the fluid may allow measurement of the interaction between the movement of the resonator and the fluid to be analyzed on the outside surface of the resonator. In some embodiments, the fluid flow path may be diverted or the resonator adapted such that interaction between the movement of the resonator and the fluid to be analyzed is on the inside surface of the resonator. In some embodiments, the resonator may be designed such that the fluid interaction occurs on both the outside and inside surfaces of the resonator.

As one of ordinary skill in the art with the benefit of this disclosure will recognize, the resonators of the densitometer may be constructed with different geometries and/or materials of construction. In certain embodiments, the geometry and material of construction of the resonators may be chosen so as to optimize the sensitivity of the resonant frequencies of the structure to changes in fluid density. In other embodiments, the geometry and the material of construction of the resonators may be chosen so that the resonant frequencies of the resonator are within a suitable frequency range for the transducers. In yet other embodiments, the geometry and material of construction of the resonators may be chosen so as to both to optimize the sensitivity of the resonant frequencies of the structure to changes in fluid density and so that the resonant frequencies of the resonator are within a suitable frequency range for the electronics and transducers.

Figure 15:
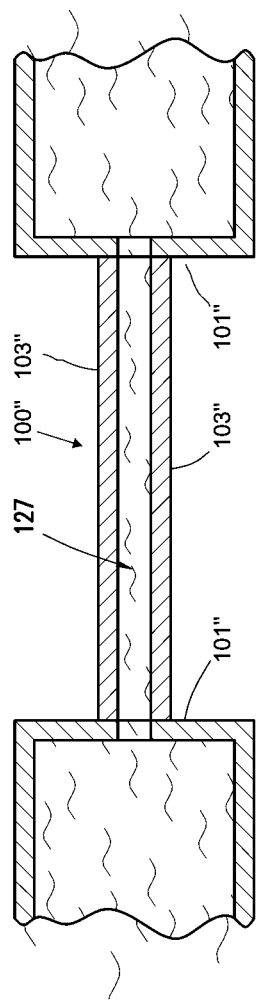
FIG. 15 depicts a resonator consistent with at least one embodiment of the present disclosure.
Figure 16:
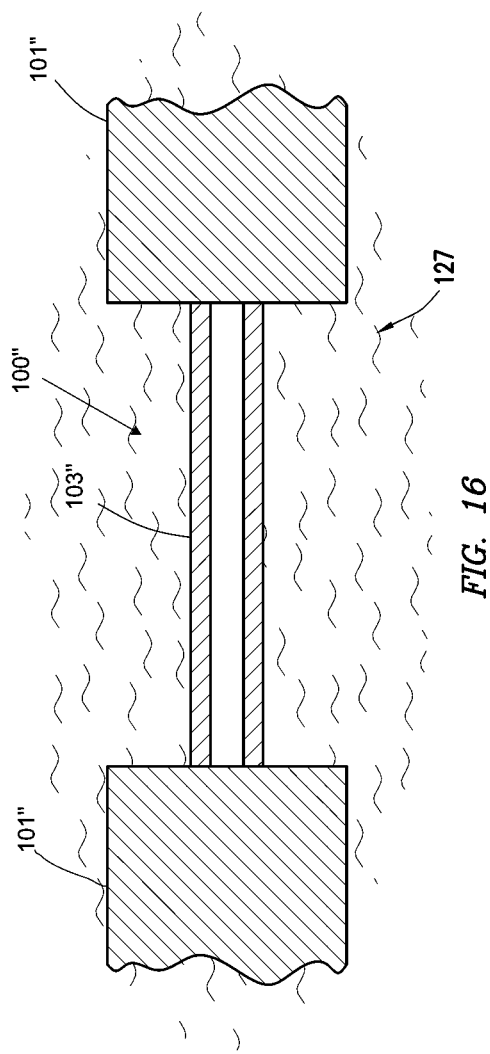
FIG. 16 depicts a resonator consistent with at least one embodiment of the present disclosure.

As shown in FIGS. 15 and 16, in some embodiments, resonator 100" may include one or more cylindrical tubes 103" through which, as shown in FIG. 15, or over which, as shown in FIG. 16 fluid 127 flows. In these embodiments, both ends of one or more cylindrical tubes 103" may be mechanically coupled to a resonator support structure 101". In certain embodiments, the resonator may include a hollow cylindrical tube 103" having a closed first end 131. The second end 130 of hollow cylindrical tube 103" may be closed or open, as shown in FIG. 17. The second end 130 of hollow cylindrical tube 103" may be mechanically coupled to resonator support structure 101". In such embodiments, closed first end 131 may be caused to move or vibrate, thereby causing interaction of resonator 100" with fluid 127.

As shown in FIG. 18, in some embodiments, resonator 100″ may include one or more resonator tines 103‴, which may be formed as elongated bars or half cylinders having first end 131′ free and second end 130′ mechanically coupled to a tine base or resonator support structure 101″. In some embodiments, as shown in FIG. 19, the one or more resonator tines 103‴ may be mechanically coupled to a resonator support structure 101″ at both ends. In some embodiments, a resonator may include only a single resonator tine. In other embodiments, one or more of the multiple resonator tines may differ from other resonator tines. In some embodiments, each of the multiple resonator tines may include identical mechanical features. In some embodiments, the use of two identical tines, may for example and without limitation, reduce the energy dissipation in resonator tines, may increase sensitivity of measurements, or may reduce the sensitivity of the densitometer measurements to external vibrations that might otherwise cause noise in or corrupt the density measurement. "Identical tines" includes tines that vary in a manner that does not substantially affect performance. In certain embodiments, identical tines may be mounted to a tine base in non-identical ways.

Figure 1B:
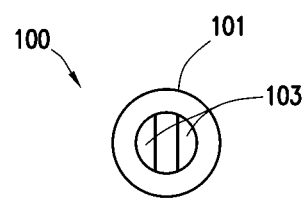
Figure 1C:
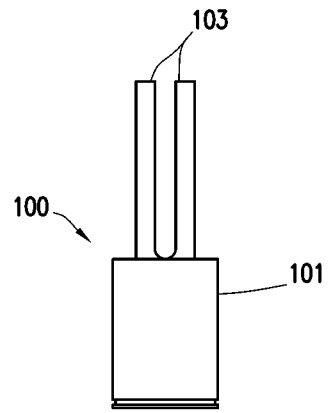

In some embodiments, as depicted in FIGS. 1A-C, tuning fork densitometer 100 may include densitometer body 101 and may include one or more resonator tines 103 mechanically coupled thereto. When tuning fork densitometer 100 is placed in a liquid, gas, or multi-phase mixture, the resonant frequency and damping factor of tuning fork densitometer 100, for instance and without being bound by theory, may be changed due to the interaction of resonator tines 103 with the fluid. One mathematical model for the tuning fork densitometer 100 may be that of a damped harmonic oscillator:

$$m\ddot{x} = F - v\dot{x} - kx$$

where m is the inertia (mass of resonator tine 103 plus the mass of the interacting fluid and certain viscosity effects, as would be understood by one of skill in the art with the benefit of this disclosure), F is the applied force, v is a damping constant related to the fluid viscosity, and k is the spring constant.

As the resonator tines 103 interact with the fluid, a virtual mass may be added to the resonator tines. A virtual mass is the mass of fluid that may be dragged by resonator tines 103 as the fluid moves past resonator tines 103. When coupled with the fluid viscosity effects, the result of the addition of the virtual mass is a change in the resonance frequency of resonator tines 103 and damping characteristics. In some embodiments and without being bound to theory, the change in resonance frequency of resonator tines 103 may be inversely proportional to the change in density. For example, as fluid density increases, more virtual mass may be added, and the resonance frequency of resonator tines 103 decreases. For example and without limitation, tuning fork densitometer 100 may have a higher resonance frequency in air then it does when immersed in water.

In some embodiments, and without being bound to theory, the fluid interaction with resonator tines 103, may cause a change in the resonant frequency of resonator tines 103, for instance, due to the added mass of the fluid and/or the influence of the fluid's viscosity. The change in the resonant frequency of resonator tines 103 may be used to determine the density of the fluid. An example of a mathematical model for the interaction of the resonator tines 103 and the fluid may be found in Groposo, et al., "Mud Density Prospection Using a Tuning Fork." J. WATERWAY, PORT, COASTAL, OCEAN ENG, 10.1061/(ASCE)WW.1943-5460.0000289, 04014047 (2014). The motion of resonator tines 103 may be described by:

$$F = -M_0\omega^2 x - \rho V_0 \omega^2 x + B_0 i\omega x + (i\omega)^{3/2} \sqrt{\mu \rho A_0 x} + K_0 x + k A_0 x$$

"F" represents the external force applied to resonator tines 103 by drive transducer 105. The first right term represents the tine inertia, where $M_0$ is the mass of resonator tines 103. The second term represents the inertia associated with the added mass that appears because the fluid surrounding resonator tine 103 is being accelerated, $V_0$ represents the volume of resonator tine 103, and ρ is the density of the fluid. The third term represents the intrinsic damping in the resonator tine 103 and densitometer 100, and $B_0$ is the tine damping coefficient. The fourth term represents the viscous damping caused by the fluid viscosity μ. The fifth and sixth terms represent elastic forces, where $K_0$ is the elasticity coefficient of the material of resonator tines 103, and k is the elasticity coefficient per unit area of the fluid in contact with resonator tines 103, and $A_0$ is a representative area. The elasticity coefficient may be related to the fluid shear modulus.

In some embodiments, a viscosity independent measurement of fluid density may be made by determining the frequency that produces a 45° phase shift above the resonant frequency of the resonator tines 103 in the fluid. In some embodiments, a viscosity measurement may be made by determining the frequencies that produce phase shifts at 45° above and 45° below the resonant frequency of the tines 103 in the fluid. In some embodiments, the difference in frequency may be approximately proportional to the square root of the viscosity.

In some embodiments, as shown in FIG. 2, densitometer 100 may include resonator electronics 109 that may provide power to, and signal conditioning for, transducers 105 and 115. In some embodiments, resonator electronics 109 may control the movement of the drive transducer 105 through an electronic drive signal that may cause movement of the resonator 103 in fluid 127. In some embodiments, resonator electronics 109 may include supporting analog and/or digital electronics to use the signals of pickup transducer 115 to observe the effect of resonator tine 103 movement in the fluid.

In some embodiments, drive transducer 105 may be electrically coupled to resonator electronics 109 to, for example and without limitation, control the drive frequency of drive transducer 105 such that a desired relationship relative to a resonant frequency of the reasonator in the fluid as measured by the pickup transducer 115 is maintained, for instance, though the density and viscosity properties of the fluid in which the sensor is immersed may change. In some embodiments, resonator electronics 109, drive transducer 105, and pickup transducer 115 may be configured and function as frequency controller, oscillator, control system, or phase locked loop circuit, such that the electronics seek either the frequency with maximum amplitude or the frequency that achieves a desired phase angle relationship between drive transducer 105 and pickup transducer 115. As a non-limiting example, the system may seek on resonance or at 45° above resonance to measure a viscosity independent density. In some embodiments, analog and digital oscillator resonator electronics 109 may output a frequency that is measured by microprocessor 119 as in FIG. 14B that is indicative of fluid density independent of viscosity. In some embodiments, the signal generated by drive transducer 105 may be generated as part of a decision or control loop in resonator electronics 109. In some embodiments, the electronics may be used to measure the frequency response of the resonator 103 (i.e. phase and amplitude vs frequency). In some embodiments, microprocessor 119 may be configured to measure only the instantaneous frequency of the frequency controller, oscillator, or phase locked loop circuit corresponding to one or more known desired points (max amplitude or 90° phase shift at resonance, 45° above and below resonance). In some embodiments, resonator electronics 109 and microprocessor 119 may be configured to record for each frequency, the system's corresponding amplitude and phase response.

In some embodiments, resonator electronics 109 may use an impulse, step, chirp signal, or other time-varying wave form to drive transducer 105. In some embodiments, resonator electronics 109 may either record or transform the time domain response of the resonator tines 103 as measured by the pickup transducer 115, from which the resonant frequencies and quality factors (frequency response) of densitometer 100 may be determined. In some embodiments, the time response of the resonator 103 as measured by the pickup transducer 115 may be analyzed by resonator electronics 109 without transformation to the frequency domain to determine fluid parameters including, but not limited to, density and/or viscosity. In some non-limiting embodiments, the resonator electronics 109 may generate a drive signal for the drive transducer 105 that may be an impulse, a single frequency, multiple frequencies, a frequency sweep, or any other suitable time variable waveform that allows for observation of the relationship between the forcing function and the resonator response. In some embodiments, resonator electronics 109 may intentionally distort or alter the drive transducer's 105 drive signal to account for non-linearity or distortion in the coupling of motion or force to the resonator 103 or to account for the dynamics of the coupling to resonator 103. In some embodiments, resonator electronics 109 may intentionally distort or alter the pickup transducer's 115 signal to similarly account for non-linearity, distortion, or the dynamics of the coupling between the resonator 103 and the pickup transducer 115.

In some embodiments, resonator electronics 109 may perform distortion or transformation of drive transducer 105 or pickup transducer 115 signals. In such embodiments, resonator electronics 109 may correct for non-linearities and/or the time and/or frequency dependent characteristics of transducers 105, 115. In some embodiments, resonator electronics 109 may convert transducer 105, 115 signals from one form to another as needed. As a non-limiting example, pickup transducer 115 may output a variable frequency that is based on the position of the resonator tines 103, with resonator electronics 109 converting pickup transducer 115 frequency output to a reading resonator position. In some embodiments, resonator electronics 109 may perform other transducer signal transformations, such as converting readings of acceleration or velocity to position, and position or velocity to acceleration.

Figure 14A:
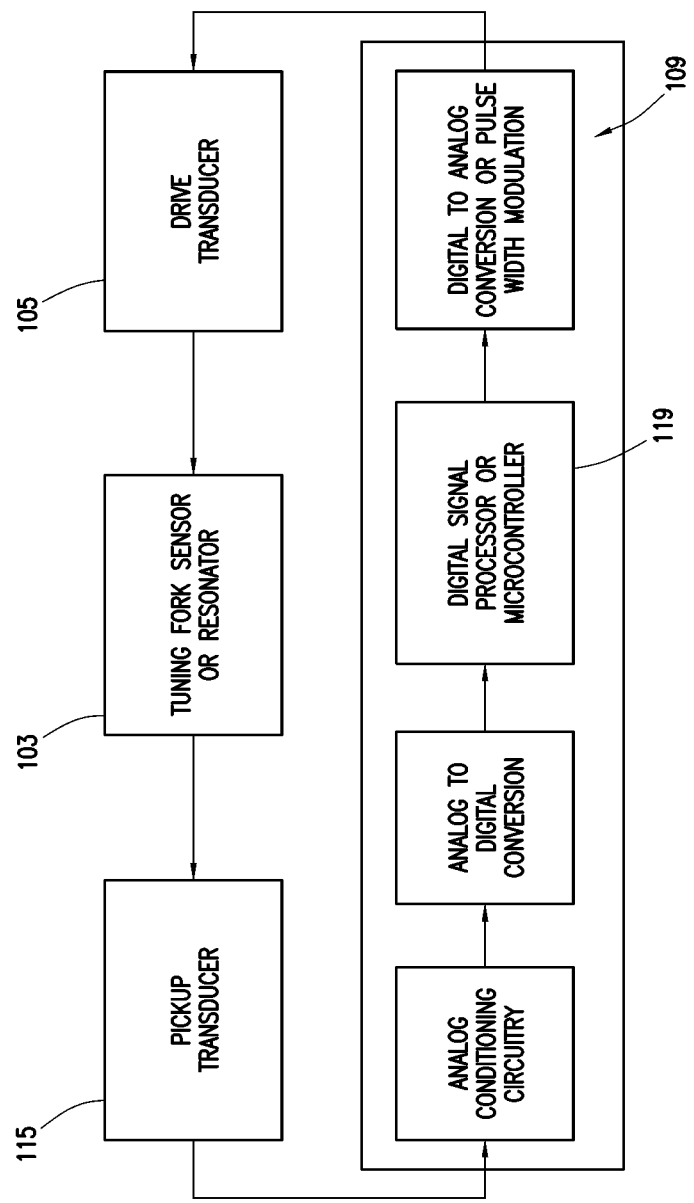
FIG. 14A depicts a block diagram of an oscillator consistent with at least one embodiment of the present disclosure.
Figure 14B:
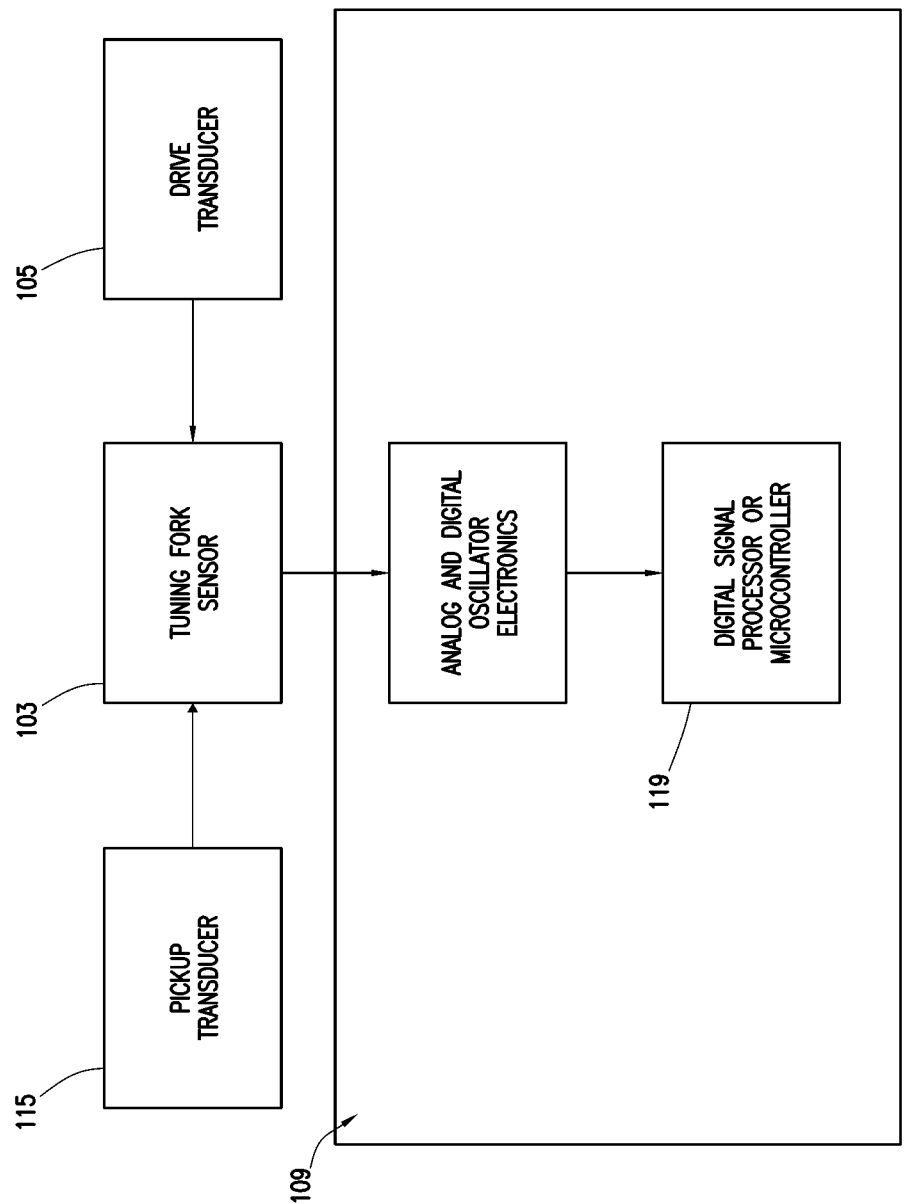
FIG. 14B depicts a block diagram of resonator electronics containing an analog oscillator subsystem whose frequency output is measured by a microprocessor consistent with at least one embodiment of the present disclosure.

In some embodiments, resonator electronics 109 may include analog electronics, digital electronics, or a mixture of analog and digital electronics. In some embodiments in which an optical pickup transducer 115 is used, resonator electronics 109 may also contain supporting optical components and opto-electronics. One having ordinary skill in the art will understand that circuit functions described in this disclosure, such as an oscillator that maintains a consistent phase relationship relative to a resonant frequency, may be constructed from analog electronics, digital electronics, or a mixture of analog and digital electronics to achieve the same functionality. A non-limiting example block diagram of an oscillator composed of analog and digital resonator electronics 109 is shown in FIG. 14A. A non-limiting example block diagram of resonator electronics 109 containing an analog oscillator subsystem whose frequency output is measured by microprocessor 119 is shown in FIG. 14B.

Figure 5:
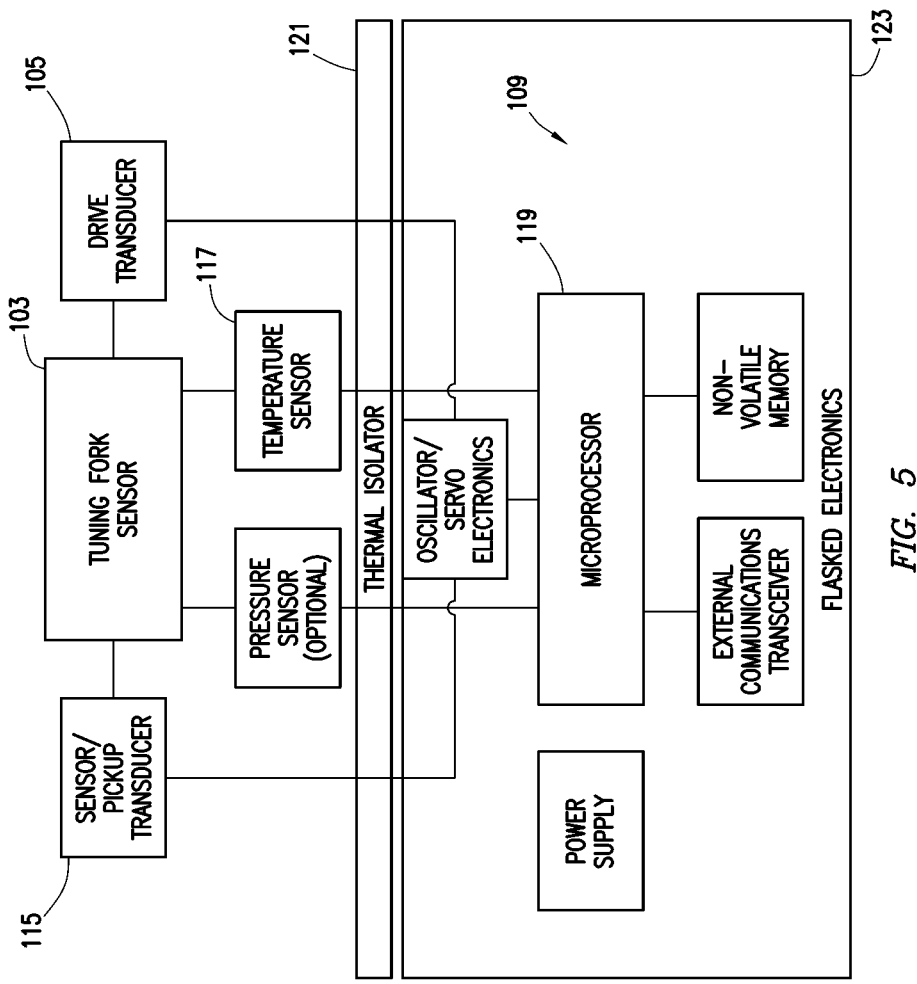
FIG. 5 depicts a block diagram of a steam quality densitometer consistent with at least one embodiment of the present disclosure.

In some embodiments, as depicted in FIG. 5, resonator electronics 109 may include microprocessor 119; however, one having ordinary skill in the art with the benefit of this disclosure will understand that one or more of a microprocessor, microcontroller, digital signal processor, ASIC, or digital logic circuits as in a FPGA or CPLD may be utilized. In some embodiments, resonator electronics 109 may also contain one or more gain control blocks to ensure that the signal levels of drive transducer 105 and pickup transducer 115 are of an appropriate level. In some embodiments, resonator electronics 109 may also contain filters. Such filters may be useful for removing noise in the system or may function as phase delay blocks.

In some embodiments, drive transducer 105 and/or pickup transducer 115 may be an active transducer in that drive transducer 105 and/or pickup transducer 115 is supplied modulation or power from resonator electronics 109. In some embodiments, drive transducer 105 and/or pickup transducer 115 may be passive in that drive transducer 105 and/or pickup transducer 115 generates an electric signal in response to movement of resonator tines 103 without an energy source beyond that of fluid 127 for drive transducer 105 or fluid 127 and/or drive transducer 105 for pickup transducer 115. In some embodiments, drive transducer 105 may be, but is not limited to, a piezoelectric actuator, rotary or linear motor, and voice coil. In some embodiments, pickup transducer 115 may be, but is not limited to, a piezoelectric sensor, rotary or linear generator, voice coil, accelerometer, gyroscope, strain gauge, capacitance sensor, Hall Effect sensor, light source and light sensitive sensor, linear or rotary potentiometer. One of skill in the art with the benefit of this disclosure with appreciate that these pickup sensors are non-limiting and other transducers may be used.

In some embodiments, one resonator tine 103 may be coupled to drive transducer 105 that provides a mechanical stimulus signal, while the other resonator tine 103 may be coupled to a pickup transducer which measures the response of the system as further discussed herein below. In some embodiments, as depicted in FIG. 2, resonator tines 103 may be mechanically coupled to drive transducer 105. In some embodiments, drive transducer 105 may be positioned within densitometer body 101. In some embodiments, drive transducer 105 may generate a force that causes resonator tines 103 to vibrate. In some embodiments, resonator tines 103 may be positioned on tine base 107 of densitometer body 101. In some embodiments, resonator tines 103 may be mechanically coupled to drive transducer 105 through one or more intermediary mechanical structures such as the tine base 107. In some embodiments, mechanical flexure of tine base 107 may cause movement of resonator tines 103. The movement of resonator tines 103 may be coupled through the tine base 107. In some embodiments, tine base 107 may be flexible such that as drive transducer 105 increases or decreases the forces thereon, those forces are coupled into the resonator tines 103, which may be deflected outward as depicted in FIG. 3A. Likewise, in some embodiments, as drive transducer 105 retracts or contracts, resonator tines 103 may return inward together as depicted in FIG. 3B, or to an original position. In some embodiments, a preload may be placed on drive transducer 105 by transducer loading mechanism 111 such that a force may be maintained on the tine base 107 when drive transducer 105 is not being actuated. In such embodiments, actuation of the drive transducer 105 may cause the drive transducer to reduce in length thereby reducing the force on the base and causing the tines to deflect inward as shown in FIG. 3B.

In some embodiments, drive transducer 105 may be formed from a piezoelectric material, as depicted in FIG. 4. As understood in the art, when an electric field is applied across a piezoelectric material, the structure may experience a change in shape. An example change in shape of drive transducer 105 due to an applied electric field is shown by the dotted lines of FIG. 4. Therefore, by applying an electric current across drive transducer 105, resonator tines 103 may be moved as described herein above.

In some embodiments, piezoelectric components, such as drive transducer 105 and pickup transducer 115, of densitometer 100 may be formed from laminated or composite structures. These laminated or composite structures may increase the capacitance of the transducer and allow for a reduction in drive voltage needed to achieve a given amount of force or conversely reduce the amount of displacement or force needed to generate a large pickup voltage. In some embodiments, the piezoelectric material used may be a piezo ceramic material with a high Curie temperature and a high piezoelectric charge coefficient. In some embodiments, the laminated piezoelectric structures may be created by appropriately layering and orienting the poled piezoelectric material 1001 with appropriately connected electrode plates 1003. In some embodiments, these layers may be held together through a compressive support structure. In some embodiments, the layers may be bonded together with conductive or non-conductive high temperature adhesives. In certain embodiments where the layers are held together with a compressive support structure, no adhesive is used.

Figure 9:
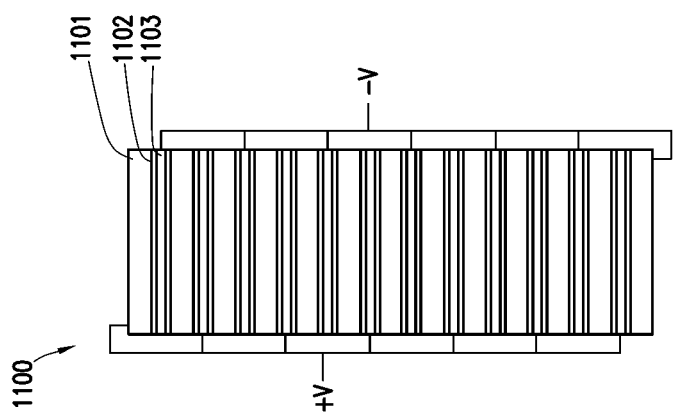
FIG. 9 depicts a transducer consistent with at least one embodiment of the present disclosure.

In some embodiments, drive 105 or pickup 115 transducers may be a vertically oriented piezoelectric transducer. For example, FIG. 9 depicts vertically-oriented piezoelectric transducer 1000. Piezoelectric elements 1001 may be arranged such that they are in parallel along a plane substantially parallel to the direction of expansion of transducer 1000. Piezoelectric elements 1001 may be plates. In vertically-oriented transducer 1000, three or more plates of high temperature piezoelectric elements 1001 are adhered to one another and electrically connected in parallel with their poling directions facing opposite directions from one another. The individual piezoelectric elements 1001 are polarized through the thickness direction prior to assembling the laminated transducer structure. High temperature electrically conductive adhesive 1002 connects each piezoelectric elements 1001 to high temperature electrically conductive electrode material 1003 which may have low coefficient of thermal expansion properties, ideally closely matching the coefficient of thermal expansion of piezoelectric elements 1001. In some embodiments, matching the coefficients of thermal expansion among materials used in transducers 105, 115 may limit thermally induced stresses inside transducers 105, 115. Electrodes 1003 may be wired together in parallel as shown schematically by lines (wires) in the figure. The drive transducer 1000 may change in shape when an electric field is applied to each set of electrodes. In some embodiments, electrodes 1003 may be formed from a high temperature, electrically conductive material with a coefficient of thermal expansion equal to or near that of the piezoelectric material such as Kovar.

Figure 10:
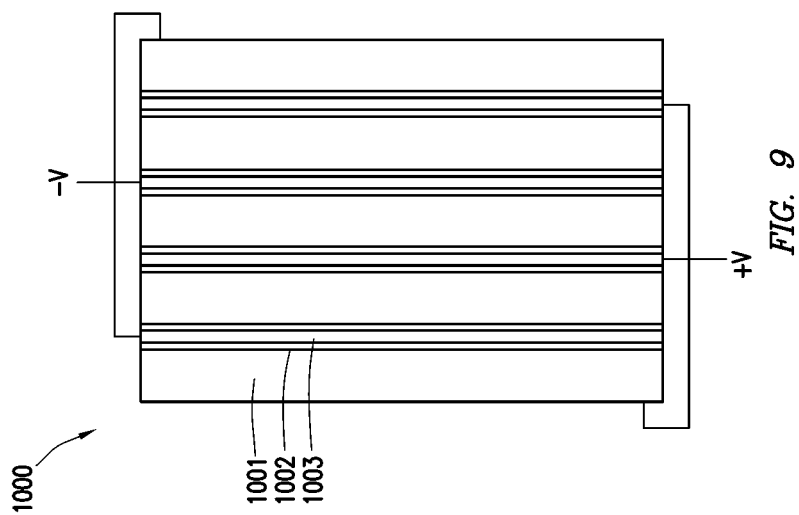
FIG. 10 depicts a transducer consistent with at least one embodiment of the present disclosure.

In some embodiments, drive 105 or pickup 115 transducers may be a horizontally oriented piezoelectric transducer. FIG. 10 depicts horizontally-oriented piezoelectric transducer 1100, where three or more plates of high temperature piezoelectric elements 1101 may be oriented horizontally and may be adhered to one another in a parallel electrical connection with their poling directions facing opposite from one another. The individual elements 1101 may be polarized through the thickness direction prior to assembling the laminated transducer structure. A high temperature electrically conductive adhesive 1102 connects each piezoelectric plate to a high temperature electrically conductive electrode material 1103 that has low coefficient of thermal expansion properties in certain embodiments closely matching the coefficient of thermal expansion of the piezoelectric material.

In some embodiments, drive 105 or pickup 115 transducers may be a series mode bi-layer pickup transducer 1300 as depicted in FIG. 11. Transducer 1300 may include two plates of high temperature piezoelectric material 1301 that may be adhered to one another with an electrically conductive high temperature adhesive 1302. Each plate of high temperature piezoelectric material 1301 may be polarized through the thickness direction and the polarization of the plates are oriented opposite from one another. Two electrical connections may be made to the outer surfaces of series mode bi-layer transducer 1300.

In some embodiments, drive transducer 105 and/or pickup transducer 115 may be a parallel mode bi-layered piezoelectric transducer 1400 as depicted in FIG. 12. Transducer 1400 may include two layers of high temperature piezoelectric material 1401 that may be adhered to one another using a high temperature electrically conductive adhesive 1402 with a high temperature low coefficient of thermal expansion electrode material 1403 sandwiched in between. Each plate of high temperature piezoelectric material 1401 may be polarized in the thickness direction and the polarity of each plate may be oriented in the same direction. The high temperature electrode material 1403 acts as an intermediate electrode where charge may be generated and measured during bending.

In applications where pickup transducer 115 converts mechanical deflection into voltage, the series mode bi-layered structure may be used instead of a parallel mode bi-layered structure. Without being bound by theory, the series mode pickup transducer may generate a higher electrical voltage (signal) when subjected to the same external force or displacement.

Figure 13:
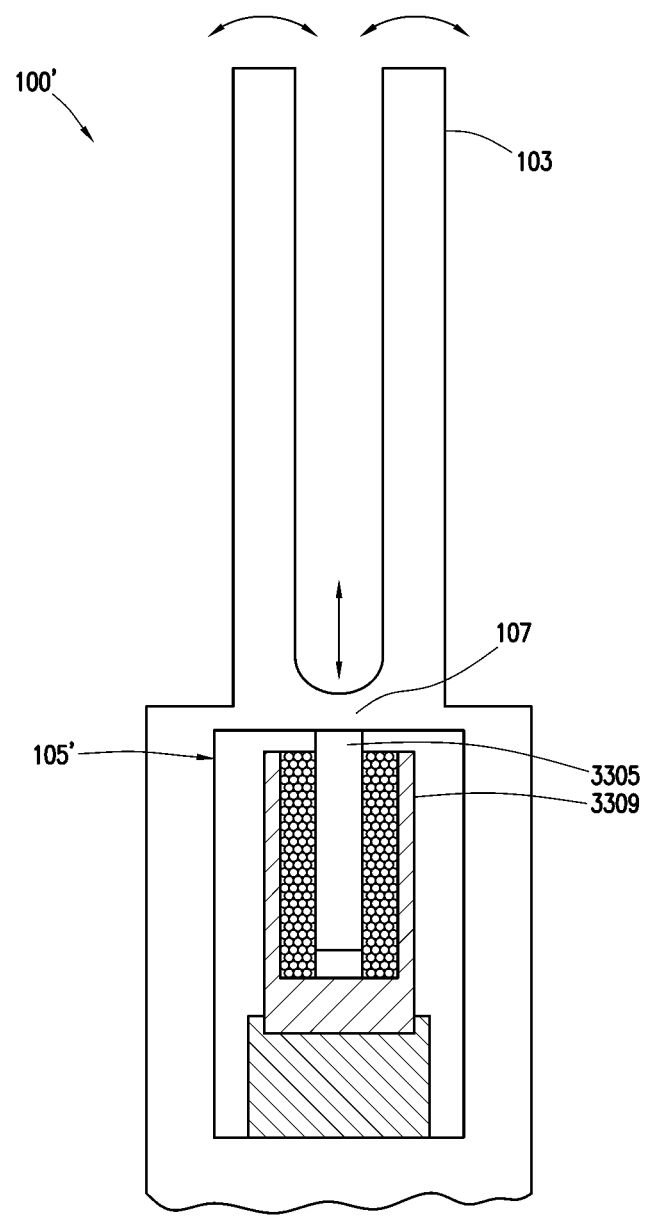
FIG. 13 depicts a cross section of a steam quality densitometer consistent with at least one embodiment of the present disclosure.

Although previously described utilizing piezoelectric transducers, one having ordinary skill in the art with the benefit of this disclosure will understand that any transducers may be utilized. For example and without limitation, as depicted in FIG. 13, densitometer 100' may include drive transducer 105'. Drive transducer 105' may be, for instance, a voice coil or solenoid. Drive transducer 105' may include an inductive coil 3309 and magnet 3305. In certain embodiments, magnet 3305 is a permanent magnet. When an electric current is passed through inductive coil 3309, a magnetic field that attracts or repels permanent magnet 3305 is generated. Magnet 3305 may be rigidly bonded or affixed to tine base 107, thereby allowing that any forces imparted on it by coils 3309 may couple into the tine base 107 and cause motion of the tines 103. In certain embodiments, using the back electromotive force (EMF) generated by coil 3309, the velocity and position of magnet 3305 may be determined and therefore the same transducer 105' may function as a pickup transducer. In an alternate embodiment, the inductive coil 3309 may instead be attached to tine base 107 and the permanent magnet 3305 rigidly bonded or affixed to the support cup. In yet another embodiment, a separate voice coil transducer 105' may be used as a pickup sensor. Magnet 3305 may be selected such that it has suitable magnetic properties at high temperatures. As a non-limiting example, a high temperature magnet material such as Samarium Cobalt may be used, allowing thereby enabling operation of the densitometer in temperatures in excess of 350° F. As previously discussed, in still further embodiments, the inductive coil drive transducer might be paired with another type of pickup transducer including but not limited to piezoelectric, Hall Effect sensor, strain gauge, capacitance sensor, accelerometer, or gyroscope.

In some embodiments, densitometer 100 may include drive transducer loading mechanism 111. Drive transducer loading mechanism 111 may, for example and without limitation, retain drive transducer 105 and apply a preload to drive transducer 105. In some embodiments, drive transducer 105 may extend between drive transducer loading mechanism 111, including support cup 113, and tine base 107. In some embodiments, drive transducer loading mechanism 111 may be movable to, for example and without limitation, adjust the compressive loading between drive transducer 105 and tine base 107. In some embodiments, the drive transducer loading mechanism 111 may be designed and constructed to achieve a predetermined preload profile on the drive transducer 105 and tine base 107 over the operable temperature range of the densitometer. In a non-limiting example, the drive transducer loading mechanism 111 may be designed to maintain a consistent preload force or minimize the variation in preload force on drive transducer 105 and tine base 107 by expanding or contracting over temperature to account for temperature dependent variations in length caused by mismatches in the coefficients of thermal expansion between the drive transducer 105, support cup 113, tine base 107, and the transducer loading mechanism elements 111.

In some embodiments, densitometer 100 may include temperature sensor 117 positioned to determine the temperature of resonator tines 103. Because resonator tines 103 are immersed in the fluid, in some embodiments the measured temperature of resonator tines 103 may be used to measure or infer the temperature of the fluid to be measured. In alternative embodiments, densitometer 100 may include temperature sensor 17 immersed in the fluid, but may also be used to measure or infer the temperature of the resonator tines 103. In some embodiments, as further discussed herein below, temperature sensor 117 may also be used to calibrate densitometer 100 or to account for changes in the response of densitometer 100 that may occur due to temperature effects. Non-limiting examples of temperature effects include changes in the resonator's natural frequencies or time response characteristics due to resonator thermal expansion and changes in the resonator material's modulus of elasticity over temperature. In some embodiments, resonator tines 103 may be constructed using one or more materials, each having its own temperature-dependent changes.

In some embodiments, temperature measurements may be combined with either a mathematical model, curve fitted calibration data, or a look-up-table to correct for temperature dependent changes in the resonator's 103 natural frequencies or time response characteristics. In some embodiments, resonators 103 and other portions of the densitometer 100 may be constructed out of a zero or extremely low coefficient of thermal expansion material such an Invar. In such embodiments, the use of such materials may eliminate the need for temperature compensation or decrease the sensitivity of the densitometer to temperature induced errors.

In some embodiments, densitometer 100 may also include a pressure sensor, depicted in FIG. 5 as pressure sensor 118, that measures the pressure of the fluid acting in and/or on the resonator tines 103. In some embodiments, the pressure may be used both in calibration and in compensating for any pressure dependent response of the resonator.

In some embodiments, densitometer 100 may be density calibrated, such as over a predefined density range. In these embodiments, density calibration may improve the accuracy of the density measurement of densitometer 100 by adjusting for non-linearities or deviations from an expected model in the densitometer's measurement within the predefined density range. In some embodiments, density calibration data points may be combined with temperature and/or pressure calibration data points, thereby creating a two or three parameter calibration and correction surface. In some embodiments, the correction surface may be approximated by a mathematical model, curve fit, or look-up-table, allowing for the correction of densitometer measurements. In some embodiments, the densitometer sensitivity to variations in temperature and/or pressure and/or density, are such that corrections may be determined independently and applied independently from one another, with the cumulative effect of all calibrations thereby improving the accuracy of densitometer 100 measurements. In some embodiments, the densitometer's sensitivity to temperature and/or pressure and/or density may be such that sensitivity to these parameters are not independently separable.

In some embodiments, temperature effects on resonator electronics 109 may be calibrated and compensated for independently from the temperature effects on the resonator 103, drive transducer 105, and pickup transducer 115. In some embodiments, resonator electronics 109 may contain a temperature sensor 117 for performing this calibration and correction.

Fluid properties such as density and viscosity may be computed when combined with sensor calibration data. Microprocessor 119 may be configured to measure and record the temperature of resonator tines 103, which when combined with temperature calibration data, may allow for computation of the change in resonance frequency due to the effects of fluid density and viscosity. These computations and the conversion of the electronic measurements, such as frequency, amplitude, and/or phase, to fluid properties may occur in real-time by microprocessor 119. In other embodiments, the computations may be logged to non-volatile storage for later retrieval and correction. In an embodiment, such computations may be accomplished by microprocessors other than microprocessor 119. Microprocessor 119 may be electrically connected to one or more other microprocessors (not shown) via a communications transceiver. In some embodiments, one of the one or more other microprocessor may serve as a master, which may periodically interrogate one or more sensor microprocessor for their readings. These readings may then be either stored local to that master microprocessor or may be conveyed to other microprocessors by various telemetry means, such as, for example and without limitation, wireline telemetry. In some embodiments, the communications transceiver may consist of only a receiver or of only a transmitter. Microprocessor 119 may be electrically connected to non-transitory computer-readable storage medium. The non-transitory computer-readable storage medium may include a database. The database may include information including, but not limited to, curve-fit data and/or thermodynamic properties of fluids. The non-transitory computer-readable storage medium may further include code instructions for determining Q, based on, for instance, fluid density, fluid temperature or pressure, and thermodynamic fluid properties.

In some embodiments, densitometer 100 may be of integrated design and construction. In some embodiments densitometer 100 may be of a modular design and construction. In some embodiments, modularity may allow for some elements of the densitometer to be easily replaced or exchanged without replacing other elements. As a non-limiting example, any or all of the following components may be exposed to high temperatures that may cause them to have a limited useful life compared to other parts of the densitometer: the tuning fork sensor 103, drive transducer 105, and pickup sensor 115, temperature sensor, and various portions of the drive transducer loading mechanism 111. In some embodiments, having a modular design and construction allows the various parts of the system to be exchanged or replaced as needed. In some embodiments, the modular elements may be mechanically fastened to each other such they can be easily replaced out in the field, district shop, or during manufacturing and calibration. In some embodiments, each modular component may be individually calibrated. Subsequently, the overall or total calibration and compensation of a densitometer measurement handled through appropriate application and combination of each modular elements calibration parameters.

In some embodiments, densitometer body 101 may be coupled directly to another structure. In some embodiments, vibration isolator 125 may couple between densitometer housing 101 and another structure, allowing, for example and without limitation, vibration isolation therebetween. Without being bound by theory, in some embodiments, vibration isolator 125 may reduce the amount of energy that would otherwise be dissipated or coupled from the drive transducer 105 into the other structure. Additionally, in some embodiments, vibration isolator 125 may reduce the coupling of vibration occurring in the other structure into the resonators 105. Non-limiting examples of vibration isolators include a stem, spring mass system, or bellows.

In some embodiments, measurement and control resonator electronics 109 may be positioned in the other structure. The transducers and temperature sensors may be connected to the measurement and control resonator electronics 109 by one or more wired connections. In some embodiments, cage 126 may be positioned about resonator tines 103 to, for example and without limitation, limit exposure of resonator tines 103 from contact or damage from debris in fluid 127. In some embodiments, cage 126 may be mechanically coupled to densitometer body 101. In certain embodiments, cage 126 may be mechanically coupled to a part of a production logging tool string. In some embodiments, cage 126 may be permeable to fluid 127. For example and without limitation, in some embodiments, cage 126 may include one or more holes adapted to allow fluid such as steam to pass therethrough. In some embodiments, densitometer 100 may include couplers (not shown) such that it can be easily removed, changed out, and reconnected to the other structure that may contain measurement and control resonator electronics 109 or additional electronics and sensors that may be used as part of a production logging tool string.

In some embodiments, densitometer 100 may include thermal isolator 121 between densitometer housing 101 and resonator electronics 109. In some embodiments, resonator electronics 109 may be run in a thermal flask 123 ("flasked"), with the flask designed to thermally isolate the contents inside the flask from what is outside the flask. In some embodiments, thermal isolator 121 functions like a flask in that thermal isolator 121 may prevent or slow down the transfer of heat from the densitometer housing 101 and fluid into resonator electronics 109. In some embodiments, the use of thermal flask 123 and thermal isolator 121 may allow for the use of standard 150° C. capable downhole electronics while other portions of densitometer 100 may be exposed to higher temperatures.

In some embodiments, high temperature electronics capable of directly withstanding the fluid temperatures encountered may be designed and constructed using high-temperature electronics components and techniques. Resonator tines 103 and drive transducer 105 may be located out of flask 123, and electrical wiring may be run through thermal isolator 121, thereby enabling connection between the transducers and resonator electronics 109. In some embodiments, the transfer of power and/or signals between resonator electronics 109 and transducers 105, 115 are made wirelessly across thermal isolator 121, for instance, electromagnetically or capacitively. In some embodiments, transducers 105, 115 may be placed inside thermal flask 123 and the thermal isolator 121, for instance, with thermally-isolated mechanical, electrical, or optical pass-throughs to allow the drive 105 and pickup transducers 115 to interact with the resonator tines 103.

Figure 6:
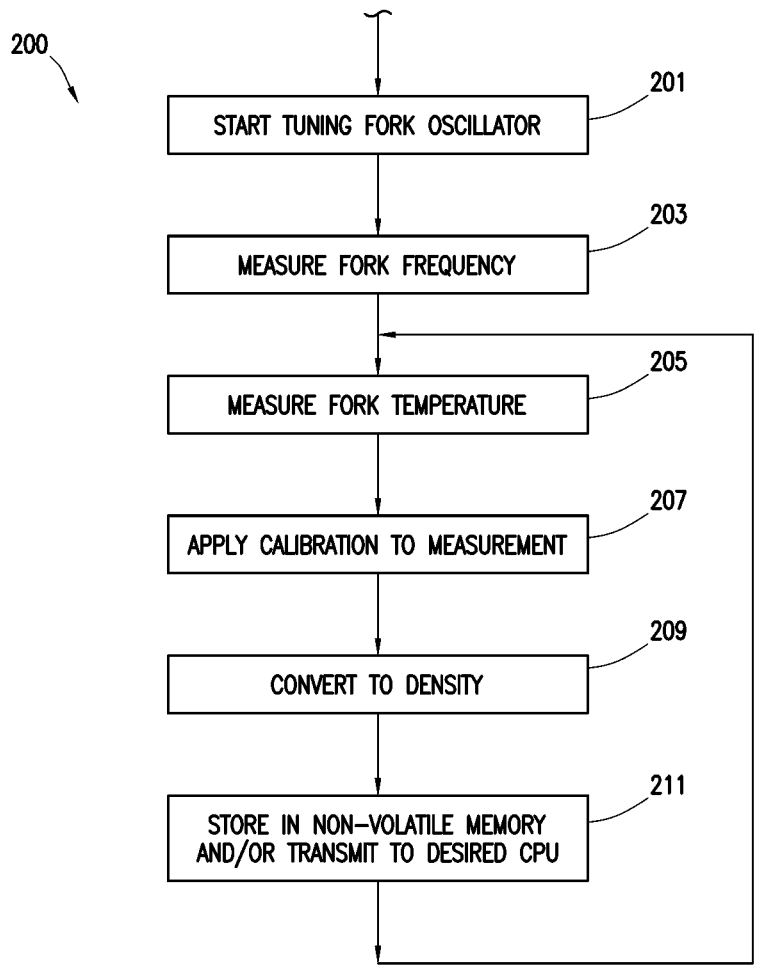
FIG. 6 depicts a flow chart of a density measurement consistent with at least one embodiment of the present disclosure.

FIG. 6 is a flow chart for densitometer operation 200 of densitometer 100 in accordance with an embodiment of the present disclosure. Resonator tines 103 may be excited by drive transducer 105 at start tuning fork oscillator 201. Resonator electronics 109 may measure the resonant frequency of resonator tines 103 using pickup transducer 115 at measure fork frequency 203. Temperature sensor 117 may be used to detect the temperature of resonator tines 103 at measure fork temperature 205. A calibration may be applied to the measurements (207), the measurements converted to a density (209), and the density may be stored or transmitted (211) as further discussed herein below. Resonator electronics 109 may therefore measure frequency and temperature of resonance tines 103, and may convert them into a calibrated density measurement.

In a wellbore, the quality of multi-phase mixtures in or flowing through the wellbore at various points along the wellbore may be determined or measured. For oil and gas wells, the gas quality may be used to assist in production of gas from a wellbore or of a gas field by improving reservoir models as well as the drilling and production programs. With knowledge of thermodynamic properties, Q may be combined with the corresponding temperature or pressure measurement of the two-phase mixture to compute the amount of heat energy or enthalpy of the mixture. At 100% Q, the mixture consists entirely of saturated vapor. Conversely, at 0% Q, the mixture consists entirely of saturated liquid.

In geothermal applications, knowledge of Q at various inflow points along the wellbore enables operators to manage producing wells, as inflow points of lower steam quality may dilute the overall quality of the produced steam. In steam flooding, cyclic steam injection, or steam assisted gravity drainage applications, knowledge of the steam quality in a wellbore can assist in distribution and injection of steam into the formation as well as production timing of oil and/or gas from the formation.

Water may exist in multiple states of phase including solid, liquid, or vapor. Steam produced, for example, from geothermal wells or industrial processes or used by, for example, industrial processes, may be "wet steam," which refers to multi-phase water that is a mixture of saturated liquid and saturated vapor. In "dry" steam, steam exists as a vapor and its thermodynamic state points may be determined from temperature and pressure measurements. However, in the wet steam, pressure and temperature are dependent. It may be desirable to ascertain of Q or a moisture parameter to determine the wet steam state point. When thermodynamic properties of a two-phase mixture are computed, those skilled in the art with the benefit of this disclosure will understand that temperature or pressure may be used. Although described herein utilizing a temperature measurement or sensor, one having ordinary skill in the art with the benefit of this disclosure will understand that a pressure sensor and its corresponding measurement may be used without deviating from the scope of this disclosure. With knowledge of thermodynamic properties, Q may be combined with the corresponding temperature or pressure measurement of the two-phase mixture to compute the amount of heat energy or enthalpy of the mixture. At 100% Q, the mixture consists entirely of saturated water vapor. Conversely, at 0% Q, the mixture consists entirely of saturated liquid water.

Certain techniques for determining Q in a borehole may include post processing of standard production logging instrumentation sensor readings of temperature, pressure, and mass/volumetric flow rates taken at different points in a wellbore. In some methods, mass and/or volumetric flow rates may be measured with a flowmeters, such as a spinner-type flowmeter. Because two-phase mixtures expands when travelling up a wellbore due to decreasing hydrostatic pressure, the quantification of inflow steam parameters utilizing production logs may be difficult to accurately measure. The production log analysis technique for evaluating Q may be based on the calculation of flow velocity and fluid holdups (the proportion of liquid in the two-phase mixture) along the wellbore. Fluid velocity may be determined from the rate of rotation of an impellor, while the fluid holdup may be derived from the fluid density along the wellbore. Fluid velocity and fluid holdup may be mathematically combined with a model of the wellbore flow, which may include friction effects, to indirectly estimate Q.

In some embodiments of the present disclosure, a method for determining Q in a wellbore may include use of an average two-phase mixture density measurement obtained from a densitometer combined with measurements of temperature or pressure and thermodynamic properties to directly determine Q.

The total volume of a mixture, V, is the sum of the volumes of the liquid and the vapor phases:

$$V = V_{liquid} + V_{vapor}$$

To obtain a relationship for the average specific volume, v, the equation above is divided by the total mass of the mixture, m.

$$v = \frac{V}{m} = \frac{V_{liquid}}{m} + \frac{V_{vapor}}{m}$$

In the two-phase mixture, the liquid phase may be a statured liquid and the vapor phase may be a saturated vapor, so $V_{liquid} = m_{liquid} v_f$ and $V_{vapor} = m_{vapor} v_g$, where $v_f$ and $v_g$ are the specific volumes for the saturated liquid and vapor phases. By substitution, $$v = \left(\frac{m_{liquid}}{m}\right) v_f + \left(\frac{m_{vapor}}{m}\right) v_g$$

$$Q = \frac{m_{vapor}}{m}$$

and may also be rearranged as $$\frac{m_{liquid}}{m} = 1 - Q.$$

Substitution then leads to the following relationship for specific volume $$v = (1-Q)v_f + Q v_g = v_f + Q(v_g - v_f)$$

Specific volumes are the inverse of the densities, and this equation may be rearranged as $$\rho = \frac{\rho_g \rho_f}{\rho_g + Q(\rho_f - \rho_g)}$$

Furthermore, this equation may be rearranged to solve for Q, in terms of average density, ρ, and the saturated liquid and vapor phase densities, $\rho_l$ and $\rho_g$, which are functions of temperature or pressure.

$$Q = \frac{\rho_g \rho_f}{\rho(\rho_f - \rho_g)} - \frac{\rho_g}{\rho_f - \rho_g}$$

Thus, for a two-phase mixture, given a temperature (or pressure) and a density (inverse of specific volume), one may directly and uniquely determine Q, thereby reducing or eliminating post-processing of the production logs and reducing interpretation variances. This equation may be reformulated in terms of the average specific volume and the specific volumes of the saturated liquid and vapor phases. Thermodynamic property data may include density or specific volume of the saturated liquid and saturated vapor phases. In some embodiments, densitometer 100 may be used to measure two-phase mixture density. The two-phase mixture may be liquid water and steam.

Is some embodiments, resonator tines 103 may include a hydrophobic coating. In some such embodiments, the hydrophobic coating may, for example and without limitation, reduce the tendency for water vapor to condense on the surface of resonator tines 103, thereby improving the accuracy of the density and quality measurements.

In certain steam quality measurement devices, a sample of a two-phase mixture flowing in a line or wellbore is diverted for testing. In some embodiments described in the present disclosure, the quality measurement device, such as, for example, densitometer 100, may not require flow diversion, as the sensing element, such as, for example, resonator tines 103, may be placed directly into the two-phase mixture or wellbore path.

In some embodiments, an apparatus for measuring Q may include densitometer 100 that may include temperature sensor 117 positioned to determine the temperature of resonator tines 103. Because resonator tines 103 are immersed in the two-phase mixture, in some embodiments the measured temperature of resonator tines 103 may be used to infer the temperature of the two-phase mixture to be measured. In some embodiments, densitometer 100 may include an additional temperature or pressure sensor to directly measure those properties of the fluid.

In some embodiments, densitometer 100 may be calibrated over different temperature and density ranges to ensure accurate readings regardless of the measurement conditions and reducing inaccuracies due to mathematical mis-modeling of the relationships between parameters.

In certain embodiments, instead of or in full or partial addition to the densitometer calibrations described elsewhere in this disclosure, accuracy of Q measurements may be improved by calibrating the density and temperature measurements of densitometer 100 at various known two-phase mixture qualities and temperatures. In some embodiments, the calibration or characterization of densitometer 100 density and temperature measurements against known two-phase mixture qualities at various temperatures may allow for the sensor to bypass the use of equation $$Q = \frac{\rho_g \rho_f}{\rho(\rho_f - \rho_g)} - \frac{\rho_g}{\rho_f - \rho_g}$$

to measure Q. In some embodiments, the calibration or characterization may result in improved accuracy of the Q measurement as the interaction of two-phase mixture on the resonator 103 may result in systematic errors in the density measurement that would otherwise cause errors in the measurement without calibration and correction. In some embodiments, Q measurements may be made by using densitometer density and temperature measurements combined with known two-phase mixture qualities and temperature, which may result in a multi-dimensional surface, curve, or relationship for steam quality. In some embodiments, densitometer 100 may be calibrated by taking measurements at different two-phase mixture densities. In certain embodiments, the frequency measured by the densitometer at the viscosity independent measurement point (+45 degrees above resonance) may be used instead of the density measurement of densitometer 100 to measure Q. In some embodiments this may be accomplished by transforming the average density in $$Q = \frac{\rho_g \rho_f}{\rho(\rho_f - \rho_g)} - \frac{\rho_g}{\rho_f - \rho_g}$$

into an equivalent expression that instead utilizes densitometer frequency. In some embodiments, transformation may be accomplished by using the measured frequency and temperature measurements to perform a calibration against known two-phase mixture qualities and temperatures as described herein.

Figure 7A:
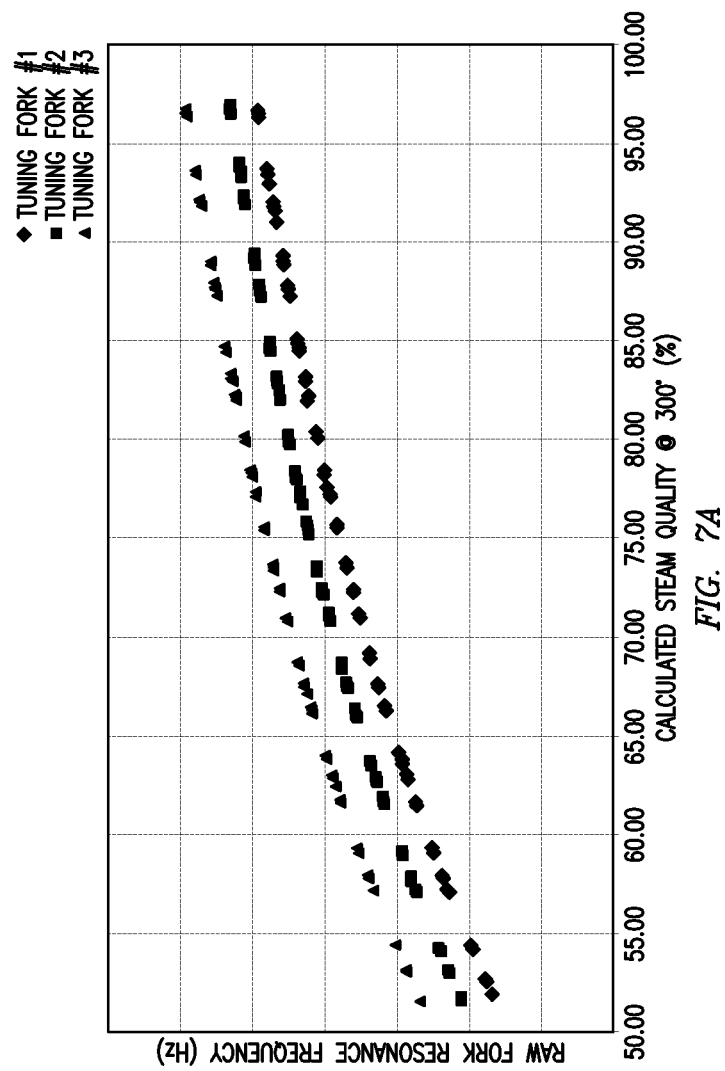
FIGS. 7A, 7B depict calibration data of a steam quality densitometer consistent with at least one embodiment of the present disclosure.
Figure 7B:
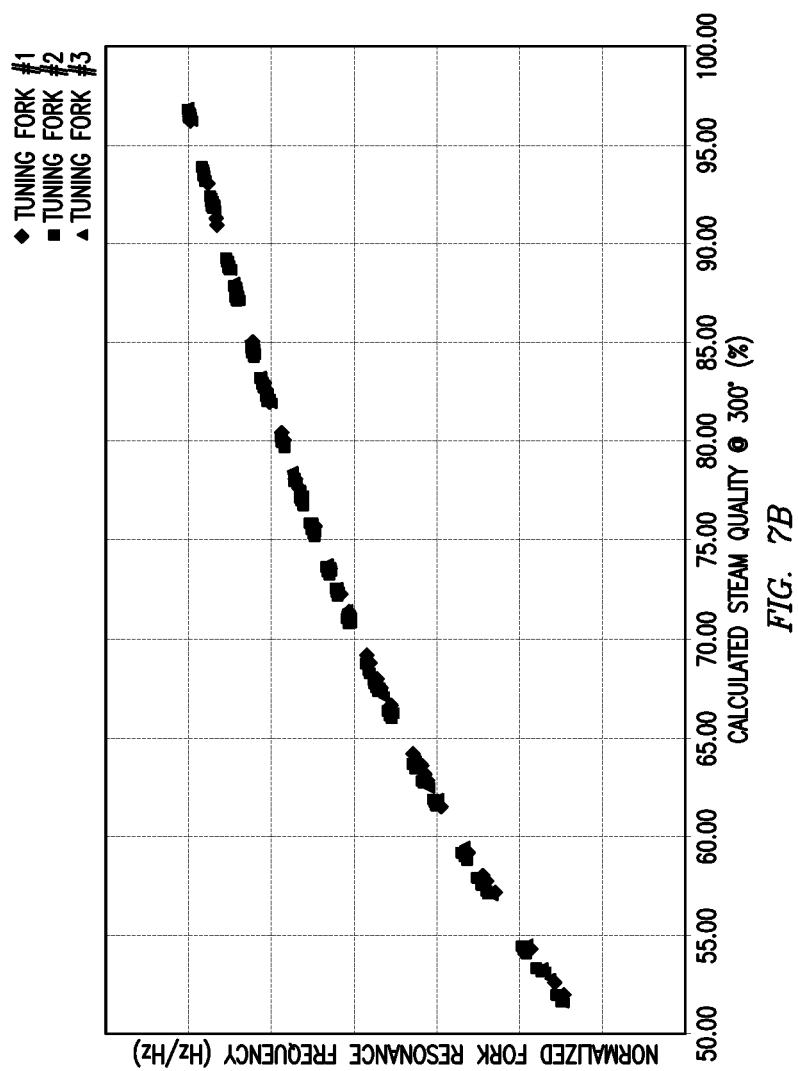

In some embodiments, calibration of densitometer 100 may be accomplished through measurements with densitometer 100 exposed to various two-phase mixture densities. In some embodiments, steam densities may be simulated by increasing or decreasing the pressure of argon gas inside a test vessel that was held nominally at room temperature. For example, in some embodiments for example and without limitation, densitometer 100 may be tested with steam qualities in the range of 50 to 95% at 300° C. FIGS. 7A, 7B show the raw and normalized resonance frequencies, respectively, obtained from the testing over the density range of interest. Variations in mechanical build tolerances result in the initial resonance frequency variations shown in the raw frequency plot of FIG. 7A. Once calibrated, the resonance frequency data from all three of the tuning forks overlay on top of each other as shown in the normalized plot of 7B. That data follows a simple trend that may be mathematically modeled and used to correct sensor errors. In some embodiments, the calibration and corrections described herein above may be performed for each densitometer 100 manufactured. In some embodiments, calibration of a densitometer design against known two-phase mixture qualities or densities may allow for a model of corrections to be developed that may then be applied to all subsequent units manufactured.

In some embodiments, the above Q equations may be implemented directly in microprocessor 119 or resonator electronics 109 to produce for display in real-time or log in memory the resultant Q measurement. In some embodiments, the density measurement may be paired with, for example, curve fit equations or look up tables to determine the saturated liquid and gas specific volumes or densities for a temperature or pressure. In an alternative embodiment, a lookup table or curve fit equations with interpolation and/or numeric optimization may be used to determine the intersection of the measured average density, temperature, and quality points. In yet other embodiments, the two-phase density and temperature or pressure readings may be stored in non-volatile memory for later processing/conversion, or may be transmitted to another microprocessor to undertake the above calculations. For example, a local production logging sensor master microprocessor or surface computer may receive the density and temperature or pressure. One skilled in the state of the art will appreciate that these embodiments are only examples and are not intended to be limiting in any way.

Referencing example, FIG. 6 which depicts a flow chart for an operation 200 of densitometer 100, for wet steam applications, further processing according to $$Q = \frac{\rho_g \rho_f}{\rho(\rho_f - \rho_g)} - \frac{\rho_g}{\rho_f - \rho_g}$$

may be implemented to convert the density and temperature measurements into Q.

Figure 8:
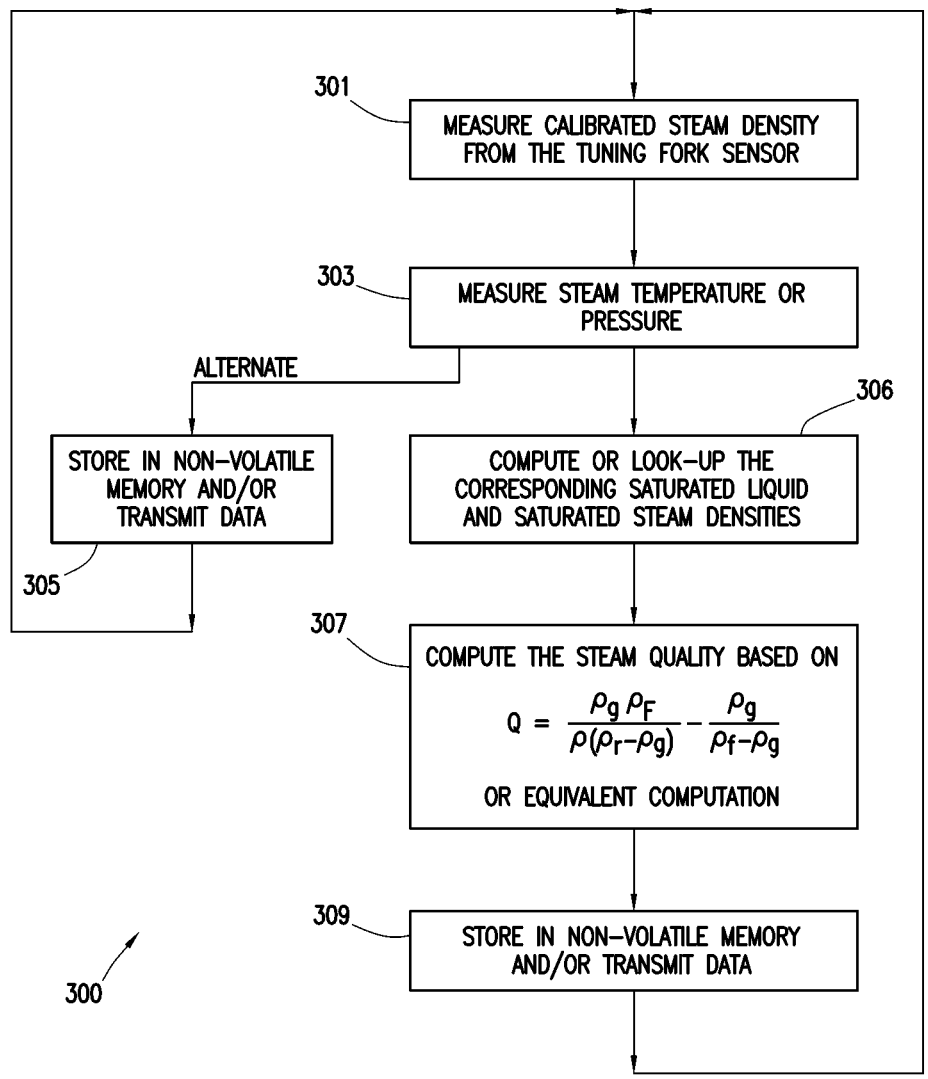
FIG. 8 depicts a flow chart of a density measurement consistent with at least one embodiment of the present disclosure.

FIG. 8 depicts an exemplary operation for obtaining steam quality 300 from density, temperature or pressure, and thermodynamic properties. At step 301 a calibrated density reading is obtained. A temperature or pressure measurement may be taken in 303. As previously described, the temperature reading may be a direct reading of the steam's temperature or may be an inferred reading of the steam's temperature based on the densitometers internal temperature sensor 117. Depending on its mode, the temperature and density may be logged for later post processing and conversion to steam quality (305), or may begin the conversion process by computing or looking up the corresponding saturated liquid and saturated steam densities (306) and computing steam quality (307). The computed steam quality may then be stored or transmitted (309). While FIG. 8 is described in terms of steam, one of ordinary skill in the art with the benefit of this disclosure will recognized that FIG. 8 and the steps therein apply to two-phase mixtures generally.

In certain embodiments, to obtain a more accurate determination of the fluid characteristics, mixer, such as a diffuser, mechanical mixer or injector may be used to form a heterogeneous two-phase fluid.

In certain embodiments, densitometer may be used to determine density as part of a downhole formation fluid sampling tool.

In certain embodiments, such as when quality or density of the fluid may be segmented, a plurality of densitometers along the wellbore may be used.

Variations in fluid property measurements over time may be used to better understand the flow characteristics. Variations in density, for example, may be indicative of two phase flow characteristics (for example—how well mixed the individual phases are). Multiple measurements may be averaged in time to produce a better estimate of bulk density.

The foregoing outlines features of several embodiments so that a person of ordinary skill in the art may better understand the aspects of the present disclosure. Such features may be replaced by any one of numerous equivalent alternatives, only some of which are disclosed herein. One of ordinary skill in the art should appreciate that they may readily use the present disclosure as a basis for designing or modifying other processes and structures for carrying out the same purposes and/or achieving the same advantages of the embodiments introduced herein. One of ordinary skill in the art should also realize that such equivalent constructions do not depart from the spirit and scope of the present disclosure and that they may make various changes, substitutions, and alterations herein without departing from the spirit and scope of the present disclosure.

What is claimed is:

1. A method for measuring two-phase mixture quality in a fluid comprising:
    providing a densitometer, the densitometer including:
        a densitometer body;
        a vibration isolator, the vibration isolator mechanically coupling the densitometer body to another structure, the vibration isolator exposed to the fluid;
        a resonator tine, the resonator tine mechanically coupled to the densitometer body;
        a drive transducer, the drive transducer mechanically coupled to the resonator tine and positioned within the densitometer body; and
        a pickup transducer, the pickup transducer mechanically coupled to the resonator tine and positioned within the densitometer body;
    exposing the resonator tine to the fluid;
    oscillating the resonator tine with the drive transducer;
    measuring the oscillation of the resonator tine with the pickup transducer;
    measuring a temperature or pressure of the fluid;
    determining a density of the fluid ρ based on the measured oscillation of the resonator tine; and
    determining a two-phase mixture quality based on the determined density according to:

$$Q = \frac{\rho_g \rho_f}{\rho(\rho_f - \rho_g)} - \frac{\rho_g}{\rho_f - \rho_g}$$

where $\rho$ is the determined density of the fluid, $\rho_f$ is the saturated liquid phase density of the fluid at the measured temperature or pressure, and $\rho_g$ is the vapor phase density of the fluid at the measured temperature or pressure.

2. The method of claim 1, wherein the densitometer further comprises a temperature sensor, and the method further comprises:
    measuring a temperature of the fluid using the temperature sensor; and
    determining the two-phase mixture quality of the fluid based at least in part on the temperature.

3. The method of claim 1, wherein the densitometer further comprises a pressure sensor, and the method further comprises:
    measuring a pressure of the fluid using the pressure sensor; and
    determining the two-phase mixture quality of the fluid based at least in part on the pressure.

4. The method of claim 1, further comprising:
    storing one or more of the measured oscillation, density, or two-phase mixture quality on a non-volatile, tangible, computer readable memory medium.

5. The method of claim 1, wherein measuring the oscillation of the resonator tine comprises measuring a frequency of the oscillation of the resonator tine.

6. The method of claim 1, wherein the two-phase mixture is two phase mixture of water.

7. The method of claim 1, wherein the determining operations are carried out by resonator electronics, and the resonator electronics comprise one or more of a microprocessor, microcontroller, digital signal processor, ASIC, FPGA, or CPLD.

8. The method of claim 1, wherein the drive transducer comprises one or more of a piezoelectric actuator, rotary or linear motor, and voice coil.

9. The method of claim 1, further comprising applying a calibration to the determined density.

10. The method of claim 1, wherein the vibration isolator comprises a stem, spring mass system, or bellows.

11. The densitometer of claim 1, further comprising a cage mechanically coupled to the densitometer body and extending about the resonator tine, the cage being permeable to the fluid.

12. A densitometer comprising:
    a densitometer body;
    a vibration isolator, the vibration isolator mechanically coupling the densitometer body to another structure, the vibration isolator exposed to a fluid measured by the densitometer;
    a resonator tine, the resonator tine mechanically coupled to the densitometer body and configured to be immersed in the fluid;
    a drive transducer, the drive transducer mechanically coupled to the resonator tine and positioned within the densitometer body; and
    a pickup transducer, the pickup transducer mechanically coupled to the resonator tine and positioned within the densitometer body.

13. The densitometer of claim 12, further comprising a temperature sensor positioned to measure the temperature of the resonator tine or a fluid.

14. The densitometer of claim 12, further comprising a pressure sensor to measure the pressure of a fluid.

15. The densitometer of claim 12, wherein the resonator tine is one of an elongated bar, or half cylinder.

16. The densitometer of claim 12, further comprising a second resonator tine.

17. The densitometer of claim 12, wherein the drive transducer and pickup transducer are the same transducer.

18. The densitometer of claim 12, wherein the vibration isolator comprises a stem, spring mass system, or bellows.

19. The densitometer of claim 12, wherein the densitometer body further comprises a tine base, the resonator tine mechanically coupled to the tine base, and the drive transducer mechanically coupled to the tine base.

20. The densitometer of claim 19, wherein the drive transducer comprises one or more of a piezoelectric actuator, rotary or linear motor, and voice coil.

21. The densitometer of claim 19, wherein at least one of the drive transducer and the pickup transducer comprises an inductive coil and a permanent magnet, wherein the permanent magnet is mechanically coupled to the tine base.

22. The densitometer of claim 19, further comprising a drive transducer loading mechanism.

23. The densitometer of claim 22, wherein the drive transducer loading mechanism comprises a support cup.

24. The densitometer of claim 19, further comprising a cage mechanically coupled to the densitometer body and extending about the resonator tine so as to protect the resonator tine from contact with debris in the fluid, the cage being permeable to the fluid.

25. The densitometer of claim 24, wherein the cage comprises one or more holes.

26. The densitometer of claim 19, wherein the pickup transducer comprises two or more piezoelectric elements.

27. The densitometer of claim 26, wherein the piezoelectric elements are electrically connected in parallel with their poling directions facing the same direction.

28. The densitometer of claim 19, wherein the drive transducer comprises two or more piezoelectric elements.

29. The densitometer of claim 28, wherein the piezoelectric elements are electrically connected in parallel with their poling directions facing opposite directions from one another.

30. The densitometer of claim 28, wherein the piezoelectric elements are arranged along a plane parallel to the direction of expansion of the drive transducer.

31. The densitometer of claim 19, further comprising resonator electronics, the resonator electronics electrically coupled to the drive transducer and the pickup transducer.

32. The densitometer of claim 31, wherein the resonator electronics comprise one or more of a microprocessor, microcontroller, digital signal processor, ASIC, FPGA, or CPLD.

33. The densitometer of claim 31, wherein the resonator electronics comprise one or more of an analog oscillator or digital oscillator.

34. The densitometer of claim 31, wherein the resonator electronics are positioned within a flask, the flask serving to thermally isolate the resonator electronics from the fluid.

35. The densitometer of claim 34, further comprising a thermal barrier between the fluid and the flask.

36. The densitometer of claim 34, wherein the vibration isolator mechanically couples between the densitometer body and the flask.

37. An apparatus comprising:
a densitometer body;
a vibration isolator, the vibration isolator mechanically coupling the densitometer body to another structure, the vibration isolator exposed to a fluid measured by the apparatus;
a resonator tine, the resonator tine mechanically coupled to the densitometer body;
a drive transducer, the drive transducer mechanically coupled to the resonator tine and positioned within the densitometer body;
a pickup transducer, the pickup transducer mechanically coupled to the resonator tine and positioned within the densitometer body;
a pressure or temperature monitor, the pressure or temperature monitor adapted to measure the pressure or temperature of a fluid;
a microprocessor, the microprocessor in electrical connection with the drive transducer and pickup transducer, the microprocessor including non-transitory computer-readable storage medium, the non-volatile memory including a database of fluid thermodynamic properties.

38. The apparatus of claim 37, wherein the pickup transducer, the drive transducer, or both is an active transducer.

39. The apparatus of claim 37, wherein the pickup transducer, the drive transducer, or both is a passive transducer.

40. The apparatus of claim 37, wherein the drive transducer is a piezoelectric actuator, rotary or linear motor, or voice coil.

41. The apparatus of claim 37, wherein the pickup transducer is, a piezoelectric sensor, rotary or linear generator, voice coil, accelerometer, gyroscope, strain gauge, capacitance sensor, Hall Effect sensor, light source and light sensitive sensor, linear or rotary potentiometer.

42. The apparatus of claim 37, wherein the vibration isolator comprises a stem, spring mass system, or bellows.

* * * * *